(12) United States Patent
Konstantino et al.

(10) Patent No.: US 10,524,952 B2
(45) Date of Patent: Jan. 7, 2020

(54) DEVICES AND METHODS FOR PRESSURE-RESPONSIVE RESHAPING OF BLOOD VESSELS

(71) Applicant: Sano V Pte Ltd, Singapore (SG)

(72) Inventors: Eitan Konstantino, Orinda, CA (US); Tanhum Feld, Moshav Merhavya (IL); Li Min Koh, Singapore (SG); Steve Wiesner, Singapore (SG)

(73) Assignee: Sano V Pte Ltd, Singapore (SG)

( * ) Notice: Subject to any disclaimer, the term of this patent is extended or adjusted under 35 U.S.C. 154(b) by 476 days.

(21) Appl. No.: 15/370,483

(22) Filed: Dec. 6, 2016

(65) Prior Publication Data

US 2017/0156916 A1    Jun. 8, 2017

Related U.S. Application Data

(60) Provisional application No. 62/299,463, filed on Feb. 24, 2016, provisional application No. 62/264,209, filed on Dec. 7, 2015.

(51) Int. Cl.
| | | |
|---|---|---|
| *A61F 2/26* | (2006.01) | |
| *A61F 5/41* | (2006.01) | |
| *A61B 17/122* | (2006.01) | |
| *A61B 17/128* | (2006.01) | |
| *A61B 17/12* | (2006.01) | |
| *A61B 17/068* | (2006.01) | |
| *A61B 17/06* | (2006.01) | |
| *A61B 17/064* | (2006.01) | |

(52) U.S. Cl.
CPC ............ *A61F 5/41* (2013.01); *A61B 17/1204* (2013.01); *A61B 17/128* (2013.01); *A61B 17/1214* (2013.01); *A61B 17/1227* (2013.01); *A61B 17/12109* (2013.01); *A61F 2/26* (2013.01); *A61B 17/068* (2013.01); *A61B 2017/06042* (2013.01); *A61B 2017/0649* (2013.01)

(58) Field of Classification Search
CPC .......... A61B 17/12013; A61B 17/1285; A61B 17/122; A61B 90/92; A61B 2090/0811; A61B 2017/00867; A61B 2017/00871
USPC ...................................... 600/30, 40
See application file for complete search history.

(56) References Cited

U.S. PATENT DOCUMENTS

| | | | |
|---|---|---|---|
| 4,958,630 | A | 9/1990 | Rosenbluth et al. |
| 5,733,295 | A | 3/1998 | Back et al. |
| 6,409,737 | B1 | 6/2002 | Fortier et al. |

(Continued)

FOREIGN PATENT DOCUMENTS

| | | |
|---|---|---|
| WO | WO-0130275 A1 | 5/2001 |
| WO | WO-2013152283 A1 | 10/2013 |
| WO | WO-2015191465 A1 | 12/2015 |

OTHER PUBLICATIONS

International search report and written opinion dated Feb. 24, 2017 for PCT Application No. US-1665214.

(Continued)

*Primary Examiner* — Samuel G Gilbert
(74) *Attorney, Agent, or Firm* — Wilson Sonsini Goodrich & Rosati (57) ABSTRACT

A device for controlling blood flow through a vein is provided. The device includes a device body configured for implantation in or around the vein. The device body is capable of reducing flow through the vein in response to an increase in tissue pressure around the vein.

11 Claims, 9 Drawing Sheets

(56) References Cited

U.S. PATENT DOCUMENTS

| | | | |
|---|---|---|---|
| 7,104,949 B2 * | 9/2006 | Anderson | A61B 17/0469 600/30 |
| 7,678,042 B2 | 3/2010 | Jackson | |
| 8,240,313 B2 | 8/2012 | Hsu | |
| 2005/0234541 A1 | 10/2005 | Hunt et al. | |
| 2005/0277907 A1 | 12/2005 | Jackson | |
| 2011/0007458 A1 | 1/2011 | Liao et al. | |
| 2011/0066226 A1 | 3/2011 | Bell et al. | |
| 2011/0066254 A1 | 3/2011 | Forsell | |
| 2011/0172692 A1 | 7/2011 | Wu | |
| 2011/0202124 A1 | 8/2011 | Mauch et al. | |
| 2012/0232569 A1 | 9/2012 | Wright | |
| 2014/0214159 A1 | 7/2014 | Vidlund et al. | |
| 2015/0173765 A1 | 6/2015 | Miller et al. | |
| 2016/0143642 A1 * | 5/2016 | Wright | A61B 17/122 606/142 |

OTHER PUBLICATIONS

Rao, et al., Vasculogenic Impotence, Arterial and Venous Surgery, Urologic clinics of north America, May 2001, 28(2):309-19.

* cited by examiner

DEVICES AND METHODS FOR PRESSURE-RESPONSIVE RESHAPING OF BLOOD VESSELS

CROSS-REFERENCE TO RELATED APPLICATION

This application claims the benefit of U.S. Provisional No. 62/299,463, filed Feb. 24, 2016, and U.S. Provisional No. 62/264,209, filed Dec. 7, 2015, the entire contents of which are incorporated herein by reference.

The disclosure of this provisional application is related to that of application Ser. No. 14/732,629, filed on Jun. 5, 2015, the full disclosure of which is incorporated herein by reference.

BACKGROUND OF THE INVENTION

1. Field of the Invention

The present invention relates to systems and methods for treating biological vessels and more particularly reshaping veins and to modify their biomechanics in order to allow a reduction in blood flow either permanently or in response to an increase in surrounding blood pressure. In particular, the present invention relates to devices and methods for treating erectile dysfunction and, more particularly, to devices for reshaping the lumen of a penile vein to reduce flow therethrough during penile tumescence.

Venous leaks include various phenomenon where changes in or around the venous system cause a noticeable clinical impact. For example, the veins have internal valves that prevent back flow and allow blood flow back to the heart in the low pressure venous system. Vascular leaks may occur as a vein diameter increases around which can inhibit valve closure (causing a venous leak). Such venous leaks may cause an accumulation of blood in the lower extremities that in turn may cause discomfort and pain. It is desirable to be able to reshape the vein with the goal of restoring the functionality of the valve.

Venous valves also play an important role in penile erection. Penile erection results from increased local blood pressure in the penis. Two corpora cavernosa located in the penis fill with blood coming from the deep arteries of the penis. Expansion of the corpora cavernosa compresses the associated outflow veins, thus inhibiting the blood outflow and allowing the increased local blood pressure to cause an erection.

In a large percentage of men over age 40, this functionality is impaired, commonly referred to as erectile dysfunction (ED). While the cause can be an insufficient inflow of blood (arteriogenic ED) in many cases the cause is the incomplete inhibition of venous outflow (venogenic ED). Incomplete venous occlusion typically results from changes in the biomechanical behavior of the veins that increase resistance to pressure.

Presently, ED has limited treatment options. Available medications typically increase blood inflow and may not be effective in men suffering from venous leak. Other treatment options usually involve a major surgery and complete occlusion of major vein, but such treatment suffers from poor long term outcomes. The failure of complete venous occlusion is believed to be caused by the development of collateral veins in response to complete occlusion of the deep dorsal vein and/or other penile veins.

As an alternative to surgery, various external compression devices have been proposed to treat ED by inhibiting blood outflow. Most such devices, however, user actuation and are uncomfortable to wear and use.

For these reasons, it would be desirable to provide procedures and devices with improved short term and/or long term results for treating ED and modulating flow through other veins. It would further be desirable to provide devices for inhibiting venous flow which may be implanted in relatively simple procedure, particularly outpatient procedures and procedures that can be performed in a doctor's office with local or no anesthesia. In particular, such devices and methods should be simple and effective for treating ED. At least some of these objectives will be met by the inventions described hereinafter.

2. Description of the Background Art

Methods and devices for treating ED and for modulating blood flow through veins and arteries are described in US Patent Publs. 2005/0277907; 2011/0066254; and 2011/007458; and U.S. Pat. No. 8,240,313. See also Rao and Donatucci (2001) Urologic Clinics 28:309-319. Devices for applying external vein compression are described in US2009/0248109 and US2011/0087337.

SUMMARY OF THE INVENTION

The present provides methods and devices for inhibiting blood flow through vasculature, particularly through veins but also finding some use in arterial flow. The methods rely on placing an implant over the blood vessel wall to reconfigure the shape of the blood vessel lumen. The implant may be introduced using a needle delivery device where the implant is carried over the needle and percutaneously released over the exterior of the blood vessel.

According to one aspect of the present invention there is provided a device for controlling blood flow through a vein comprising a device body configured for implantation in or around the vein, the device body being capable of reducing flow through the vein in response to an increase in tissue pressure around the vein.

According to further features in preferred embodiments of the invention described below, the device body is an open or closed ring configured for implantation around the vein.

According to still further features in the described preferred embodiments the ring is sized and shaped such that the increase in tissue pressure adjacent to the vein changes an orientation of the ring with respect to a longitudinal axis of the vein.

According to still further features in the described preferred embodiments the ring is configured for changing the orientation with respect to the longitudinal axis of the vein when the force is applied to opposing ends of the ring.

According to still further features in the described preferred embodiments the device body includes an elastically deformable element configured for implantation within the vein.

According to still further features in the described preferred embodiments the element includes two substantially planar arms being capable of angling with respect to each other in response to the increase in tissue pressure around the vein.

According to still further features in the described preferred embodiments a flow limiting capability of the element increases when the arms are angled with respect to each other.

According to still further features in the described preferred embodiments a shape of a lumen of the vein is modified by angling of the substantially planar arms with respect to each other.

According to still further features in the described preferred embodiments the arms are substantially oval loops.

According to still further features in the described preferred embodiments the arms are formed from a looped Nitinol® wire.

According to still further features in the described preferred embodiments the vein is a dorsal vein and the tissue is penile corpus cavernosa.

According to still further features in the described preferred embodiments the increase in tissue pressure results from penile tumescence.

According to another aspect of the present invention there is provided a system for controlling blood flow through a vein comprising the device described herein and a delivery device for delivering the device into or around the vein.

According to still further features in the described preferred embodiments the device body is configured as a spring selected capable of compressing in response to a force imparted thereupon by the tissue around the vein.

According to yet another aspect of the present invention there is provided a system for controlling blood flow through a vein comprising: (a) a clip being size and configured for clamping a region of the vein when positioned therethrough to reduce blood flow through the vein; and (b) a delivery device for penetrating tissue overlying a vein and delivering the clip through the walls of the vein.

According to still further features in the described preferred embodiments the clip includes two elements for flanking the vein interconnected through the vein via an intravascular region (linker).

According to still further features in the described preferred embodiments at least one of the elements includes a tissue piercing end.

According to still further features in the described preferred embodiments at least one of the elements is elastically compressible.

According to still further features in the described preferred embodiments the clip includes two spring regions linked via a linear strut.

According to still further features in the described preferred embodiments the clip is fabricated from a shape memory material capable of assuming a tissue compressive shape following delivery.

According to still further features in the described preferred embodiments the tissue compressive shape is a coil and the clip assumes a substantially linear configuration when disposed in the delivery device. A substantially linear configuration means that clip will occupy a small diameter to facilitate delivery while it may increase in length.

According to still further features in the described preferred embodiments the clip is configured for facilitating collapse of the vein under external pressure applied thereto.

According to yet another aspect of the present invention there is provided a method of controlling blood flow through a vein comprising: (a) delivering a clip having two ends interconnected via an intravascular region (linker) through walls of the vein such that the ends of the clip abut opposing outer walls of the vein with the linker positioned through the vein; and (b) compressing the clip to thereby clamp the region of the vein and reduce flow therethrough.

The present invention successfully addresses the shortcomings of the presently known configurations by providing devices for treating erectile dysfunction that can be implanted using minimally invasive surgery and do not require manual activation or implanted actuators for operability.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 2A-2B illustrate self-repositioning of an open ring implant embodiment of the present device when the fluid pressure of tissue around the vein increases (indicated by arrows).

DETAILED DESCRIPTION OF THE INVENTION

The present invention is of a device which can be used to treat erectile dysfunction. Specifically, the present invention can be used to reduce out flow through a penile vein, such as the dorsal vein, during penile tumescence thereby enabling an individual to achieve and maintain a full erection.

The principles and operation of the present invention may be better understood with reference to the drawings and accompanying descriptions. As used herein the term "about" refers to ±10%.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The Device:

Devices for treating erectile dysfunction are well known in the art. Such devices are implanted in or around the dorsal vein and are remotely actuated by the user to temporary reduce blood outflow from the penile corpus cavernosa. Due to their complicated nature, such devices can be difficult to implant and actuate while being unreliable and prone to failure.

While reducing the present invention to practice, the present inventors set out to provide a device which does not require user actuation or complex implantation procedures while offering a permanent and reliable solution to the problem of erectile dysfunction As is further described herein, embodiments of the present device are configured to reduce outflow through a vein when the pressure surrounding the vein increases as is the case with tumescence.

Thus, according to one aspect of the present invention there is provided a device for treating erectile dysfunction. As used herein, the phrase "erectile dysfunction" refers to an inability to achieve or sustain an erection suitable for sexual intercourse One aspect of the present device includes a device body which is configured for implantation in, through or around a vein, such as the penile dorsal vein, which drains the penile corpus cavernosa for the treatment of erectile dysfunction. The device body is configured capable of reducing flow through the vein preferably in response to an increase in tissue pressure around the vein Penile erection is triggered by the parasympathetic division of the autonomic nervous system (ANS), causing nitric oxide (a vasodilator) levels to rise in the trabecular arteries and smooth muscle of the penis. The arteries dilate causing the corpora cavernosa of the penis (and to a lesser extent the corpora spongiosum) to fill with blood increasing the hydrostatic pressure applied by these tissue to veins running therethrough. Tumescence is maintained by the ischiocavernosus and bulbospongiosus muscles which compress the veins of the corpora cavernosa restricting the egress and circulation of this blood.

In erectile dysfunction, the corpus cavernosa (and to a lesser extent the corpora spongiosum) are engorged with blood, however, failure to prevent egress of blood through the veins leads to loss of tumescence.

The present invention leverages tumescence and the increase of (hydrostatic) pressure applied to the veins by the tissues surrounding or adjacent to the veins to reduce outflow of blood through the veins.

To enable such functionality, the present device may include any or all of the following features:

(i) the device may be sized and configured for implantation in, through or around one or more veins or vein segments;

(ii) the device may change shape or orientation in response to an increase in tissue pressure against the vein;

(iii) the device may comprise segments, such as arms, struts, bars, flanges, pads, or the like, that apply pressure on the vein tissue to completely or partially collapse the blood vessel lumen to occlude blood outflow either temporarily during erection or constantly; and (iv) the device may be deliverable via a minimally invasive procedure.

Several configurations of the present device are envisaged herein. A device for implantation around the vein can be configured as an open or closed ring for fully or partially encircling a vein segment. Such a device can change its orientation with respect to the longitudinal axis of the vein when pressure on the vein increases. The change in device position can kink or compress the vein thereby reducing the cross sectional area through which blood flows.

A device implanted within the vein lumen can include coils, brush-like fingers or flaps that change in orientation or configuration when the pressure on the vein increases. Such changes cause the device to occupy a larger cross sectional area thereby reducing flow through the vein.

A device for implantation through the vein can include coils or clips which compress (flatten) the vein upon an increase in pressure thereon. Alternatively the device can compress (flatten) the vein constantly due to the internal spring force of the clip.

Regardless of device type, the change in configuration or orientation of the device can be gradual through increase in pressure, i.e. the change in device orientation or configuration follows the increase in pressure or it can be 'bi-phasic', i.e. the device changes from a first configuration to a second configuration once a threshold pressure is applied to the vein The device will apply an "activation" pressure sufficient to achieve at least partial closure of the lumen of the target vein or artery, typically approaching or exceeding the local blood pressure in the vessel being treated. Usually, the applied pressure should be below that which will cause damage to the vessel and/or the surrounding tissue.

The present device can be fabricated from any material including polymers and alloys. The present device can be fabricated from shape memory materials to facilitate implantation through, for example, a needle. In such cases, the device can be linearized or tightly coiled for delivery, and once released from the needle around, through or within the vein it assumes it active shape.

FIGS. 1A-3B illustrate several embodiments of the present device which is referred to herein as device 10

Figure 1A:
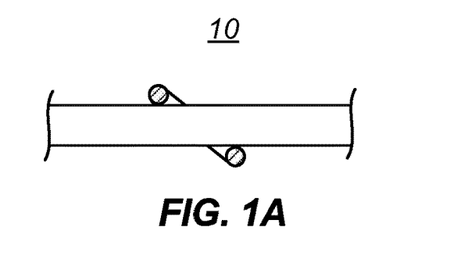
FIGS. 1A-1B illustrate self-repositioning of a closed ring implant embodiment of the present device (shown in side view) when the fluid pressure of tissue around the vein increases (indicated by arrows).
Figure 1B:
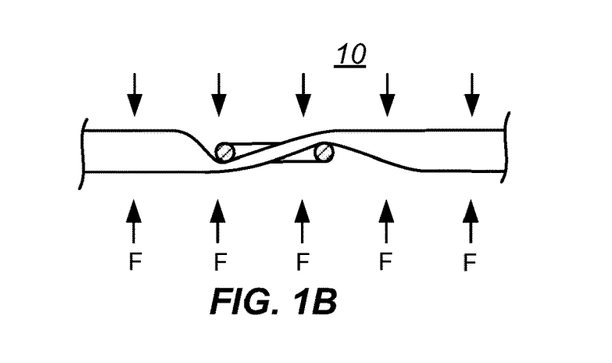

FIGS. 1A-B illustrate a closed ring embodiment of device 10 for implantation around a vein. FIG. 1A illustrates device orientation with respect to the longitudinal axis of the vein when tissue pressure is at normal non-tumescent pressure (typically about 10 to 15 mmHg, but varying among patients). The device is implanted such that is oriented at about 45 degrees with respect to the longitudinal axis.

FIG. 1B illustrates device orientation with respect to the longitudinal axis of the vein when tissue pressure (indicted by arrows) rises above normal pressure. Rotation of the device gradually decreases the lumen cross sectional area and in turn decreases outflow through the vein. As outflow decreases, tumescence increases and the pressure on the vein increases still, thereby further rotating the ring and decreasing the cross sectional area. At pressures of 25 to 40 mm Hg or above, the device 10 is nearly parallel to the longitudinal axis of the vein (FIG. 1B, typically decreasing flow by about 20% to 100%.

Once sexual arousal subsides, the arteries feeding the tissue (corpus cavernosa) constrict and tumescence decreases thereby decreasing pressure on the vein and enabling ring-like device 10 to rotate back to the non-occlusive position (FIG. 1A).

The activation force of such a ring-like device is dependent on the lever length, i.e. the distance between the ring segments that are above and below the vein. This distance also determines the angle between the vein and the ring. A sharper angle will result in higher occlusive force on the vein. On the other hand it is desirable to make the ring as small as possible to facilitate less invasive procedure. In a preferred embodiment the ring can be about 5-10 in diameter with a round cross section and a round shape. The round cross section has a diameter of about 0.1-0.5 mm. The angle between the vein and the ring can be 45 degrees or less (e.g. 30 degrees) with respect to the longitudinal axis of the vein.

Figure 2A:
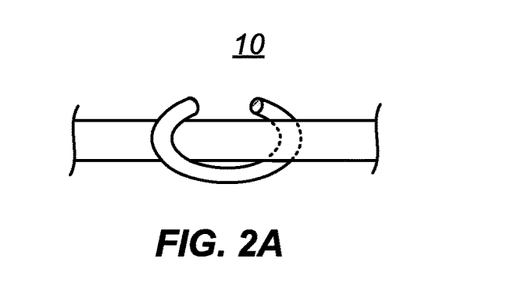
FIG. 2A is a top view of the device around the vein.
Figure 2B:
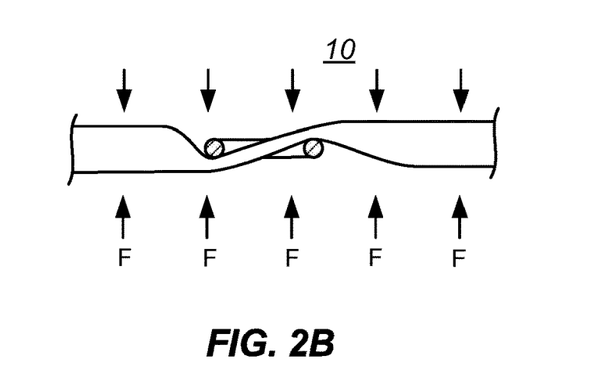
FIG. 2B is a side view.

An open ring configuration of device 10 is shown in FIGS. 2A-B. The open ring configuration functions in a manner similar to that of device 10 shown in FIGS. 1A-B (closed ring). The open ring configuration of device 10 is advantageous in that an open ring fabricated from a shape memory material (e.g. Nitinol®) can be easily linearized and delivered through a needle to self-assume its active shape following delivery. Thus, the open ring is more practical for facilitating easy placement around the vein without trauma to the vein. It can be made of polymer or metal either elastic or super-elastic. It can be inserted and place around the dorsal vein via a small incision in the penile skin and fascia.

The advantages of the ring and open ring approach are that they are positioned external to the vein (thus external to the blood stream) and operate as a temporary restrictor of flow without risk of thrombus formation. The disadvantage is that this type of device is harder to deliver, i.e. cannot be delivered via needle, and require a bigger incision in the penile.

Figure 3A:
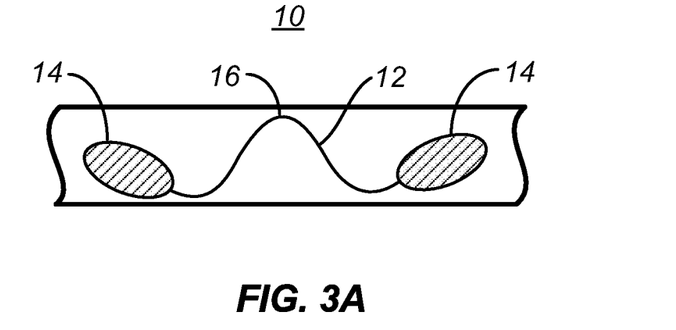
FIGS. 3A-3B illustrate device self-repositioning of an internal flap embodiment of the present device (shown in side view) when the fluid pressure of tissue around the vein increases (indicated by arrows).
Figure 3B:
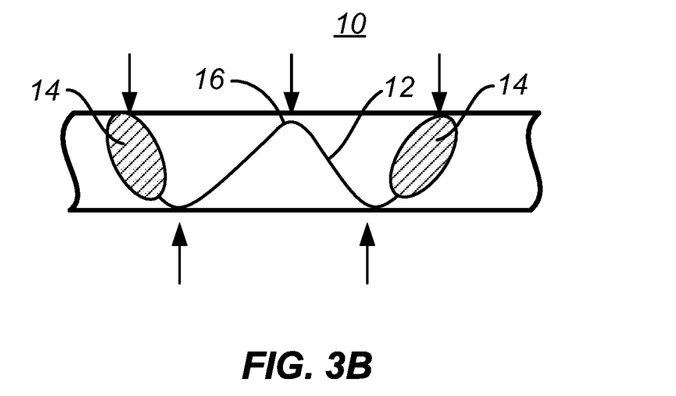

FIGS. 3A-B illustrate a device 10 configured for vein intraluminal implantation. Device 10 includes an elastically deformable element 12 attached to one or more substantially planar arms 14 being capable of angling in response to an increase in tissue pressure around the vein. In the configuration shown in FIGS. 3A-B, elastically deformable element 12 is a shaped wire (stainless steel or Nitinol or polymer) which includes a deformable hump region 16 capable of partially flattening in response to an increase in (perpendicularly oriented) pressure on the vein (shown by arrows). As region 16 flattens, arms 14 change orientation with respect to the axis of flow through the vein thereby increasing the surface area of arms 14 exposed to flow through the vein. Such a change in orientation of arms 14 can decrease flow through the vein by 20% to 100%. Once sexual arousal subsides, the arteries feeding the tissue (e.g. corpus cavernosa) constrict and tumescence decreases thereby decreasing pressure on the vein and deformable element 12. Arms 14 rotate back to the position shown in FIG. 3A and the flow through the vein increases.

Arms 14 can be configured as membrane-covered rings/ovals (as shown in FIGS. 3A-B), in which case, arms 14 are fabricated as wire loops with a polymeric membrane glued thereupon. Any configuration exhibiting an increase in resistance to flow as a result of a change in orientation (angle with respect to flow) can be used with this configuration of device 10. For example, arms 14 can be fabricated as a wire brush, as a series of overlapping helical loops, a wire mesh and the like which enable flow when positioned at a first angle with respect to flow and restrict flow when positioned at a second angle with respect to flow. Some configurations, such as the one shown in FIGS. 3A-B, restrict flow when arms 14 shift from a relatively sharp angle (e.g. 45 degrees or preferably less with respect to flow) to a relatively acute angle (more than 45 degrees, preferably nearly 90 degrees with respect to flow). As is mentioned above, such a shift exposes more of the arm 14 surface area to flow. In other configurations (e.g. mesh) flow can be restricted by an opposite shift, i.e. flow is enabled when the mesh is oriented at an acute angle (e.g. 90 degrees) with respect to the flow and restricted when the mesh is oriented at a sharp angle (e.g. 45 degrees) with respect to flow. This is due to the fact that the mesh openings decrease in size when angled with respect to flow.

In other configuration the device (the implant) is typically in the shape of a coil or spring and is configured to be inserted through the blood vessel and deployed with one or more coils underneath the blood vessel and coils over the blood vessel. The pitch between the coils is very small, usually but not necessarily in the range from 0 mm to 0.2 mm. Thus, when the device is released, the vessel is compressed between the coils underneath the blood vessel and the coils over the blood vessel, narrowing (reducing the available flow of the blood vessel which in turn reduces the blood flow. The coil is typically made of an elastic alloy, preferably Nitinol®, alternatively being formed from a stainless steel, cobalt or other alloy. The coil wire is usually round but alternatively could have a square, triangular or other cross-sectional profile. The coil wire will typically have a diameter or width in the range from 0.1 to 0.5 mm, usually being in the range from 0.1 mm to 0.2 mm. The coil will typically have a diameter in the range from 1 mm to 4 mm, usually in the range from 1 mm to 2 mm. The number of turns in each coil will typically be in the range from 2 to 10, usually from 2 to 4.

The foregoing relates to devices which are capable of changing shape in response to an increase in pressure and are thus temporarily occlusive, i.e. once arousal subsides, the devices are designed to restore near-normal flow through the vein.

The present inventors also contemplate use of devices which reshape the vein lumen (to partially reduce flow) while facilitating further vessel lumen reshaping (collapse) under external pressure (manual or hydrostatic).

Such a device (also referred to herein as a clip) can include a combination of intravascular and extra vascular elements. It can be delivered using a delivery apparatus that pierces the penile tissue and venous wall(s). The device may be temporarily or permanently implanted in the vein based on the need to the patient as determined by the physician.

The device can be initially constrained by the delivery apparatus and upon release therefrom assume an unconstrained shape which compresses the vein without completely blocking blood flow, i.e. the device forces the vessel to change its shape from an approximately cylindrical shape to a less cylindrical (e.g. oval shape or a FIG. 8 shape).

Such a shape change facilitates further vessel collapse under external pressure from the surrounding tissues during tumescence. Thus, in effect, the device preload the vein and modifies the moment of inertia of the venous walls making the vein more susceptible to bending, collapsing or compressing under an increase in external pressure. Thus, while the initial shape change of the vein caused by implantation of the device decreases blood flow through the vein, the rise in external forces further collapses the vein and further decreases or completely blocks blood flow therethrough.

The wire can be straightened and constrained in a needle type delivery apparatus. The needle pierces a superficial target vessel allowing for a release of the device inside the blood vessel while anchoring one or both ends to the vein wall or outside the vein wall. Once released, the vein wall anchored device assumes its free shape thereby shortening and forcing the vein lumen to ovalize making it more susceptible to collapse in the direction of its short axis. Thus, under external forces (manual compression or increase in blood flow in the area), the vein collapses and the blood flow decreases or stops.

The device can be configured as a wire or a ribbon having a non-constrained (free) shape that includes a central (intravascular/linker) portion which is linear, S or C shaped. The device includes end portions for anchoring to a vein wall as one or more locations. The non-constrained length of the intravascular portion of the device is shorter than the diameter of a fully open vein resulting in vein ovalization following implantation.

The device can be sized for reshaping a vein of any diameter. For example, when implanted in a 2 mm diameter vein, the device can be sized to reshape the vein lumen to form an oval with a diameter (in the direction of implantation) of 1.8 mm, 1.5 mm, 1 mm or 0.5 mm or until opposing walls of the vein come into contact creating a FIG. 8 shape.

A device suitable for compressing a 3 mm vein can have a non-constrained length of 2.5 mm. This device can be straightened to a linear wire constrained and stored, preloaded, in a small gauge needle. When straightened the length of the device can be 5-10 mm depending on non-constrained shape of the device (spiral, S-shaped etc). The distal end of the device can be released extravascularly embedding an anchor point further away from the delivery apparatus. As the delivery apparatus retracts the device proximal end will be release out of the vein forming a spring like shape compressing the vein into an oval shape. In this case only the central device portion is released inside the vessel with minimal footprint exposed to blood flow.

For small superficial or semi superficial vessels the device can be delivered through a small gauge needle or a small diameter extra vascular delivery apparatus. External guiding such as ultrasonic transducers or imaging or other known methods can be used to guide the delivery apparatus to the target vessel.

Figure 4A:
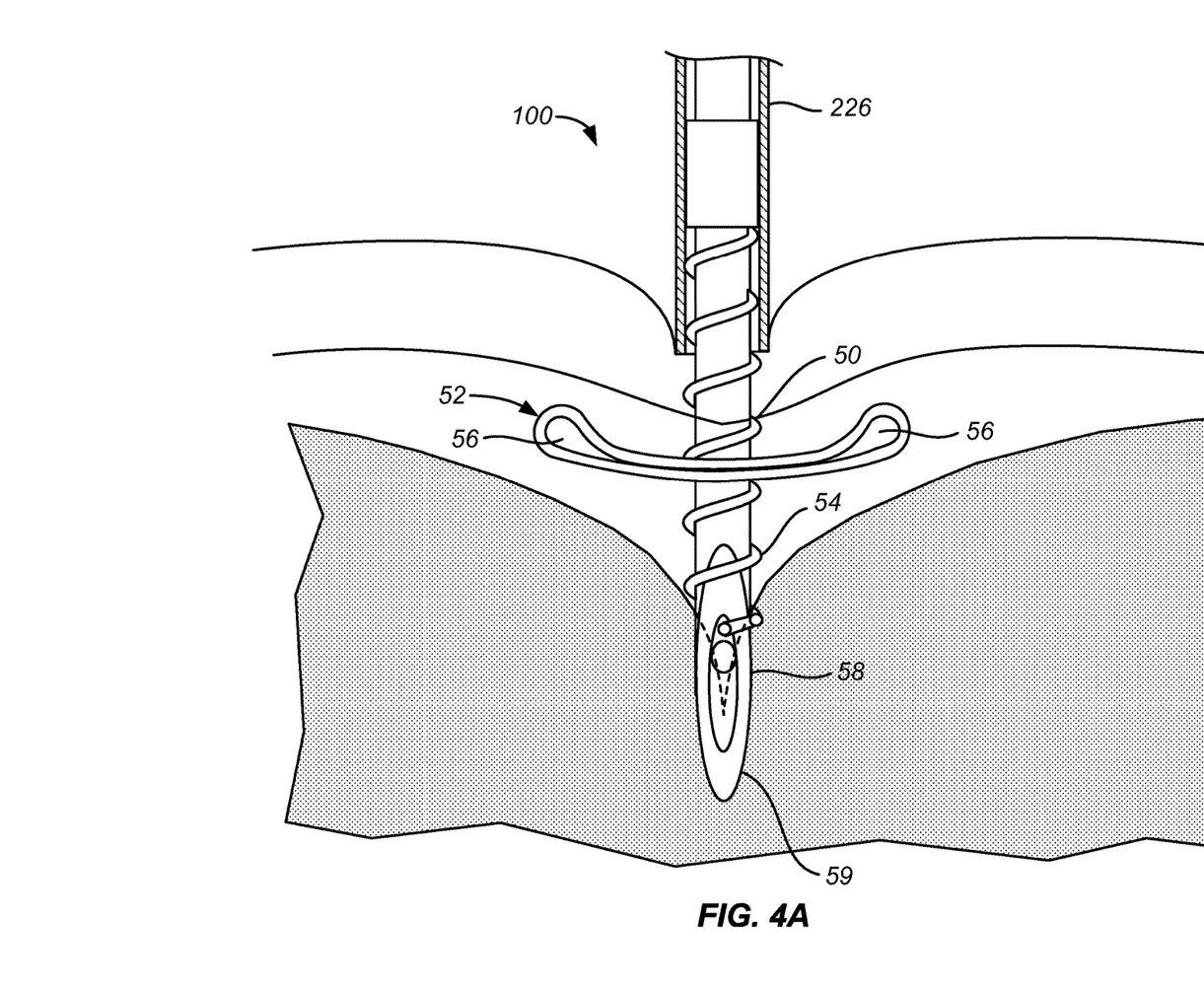
FIGS. 4A and 4B illustrate a compression implant before and after the implant is delivered.
Figure 4B:
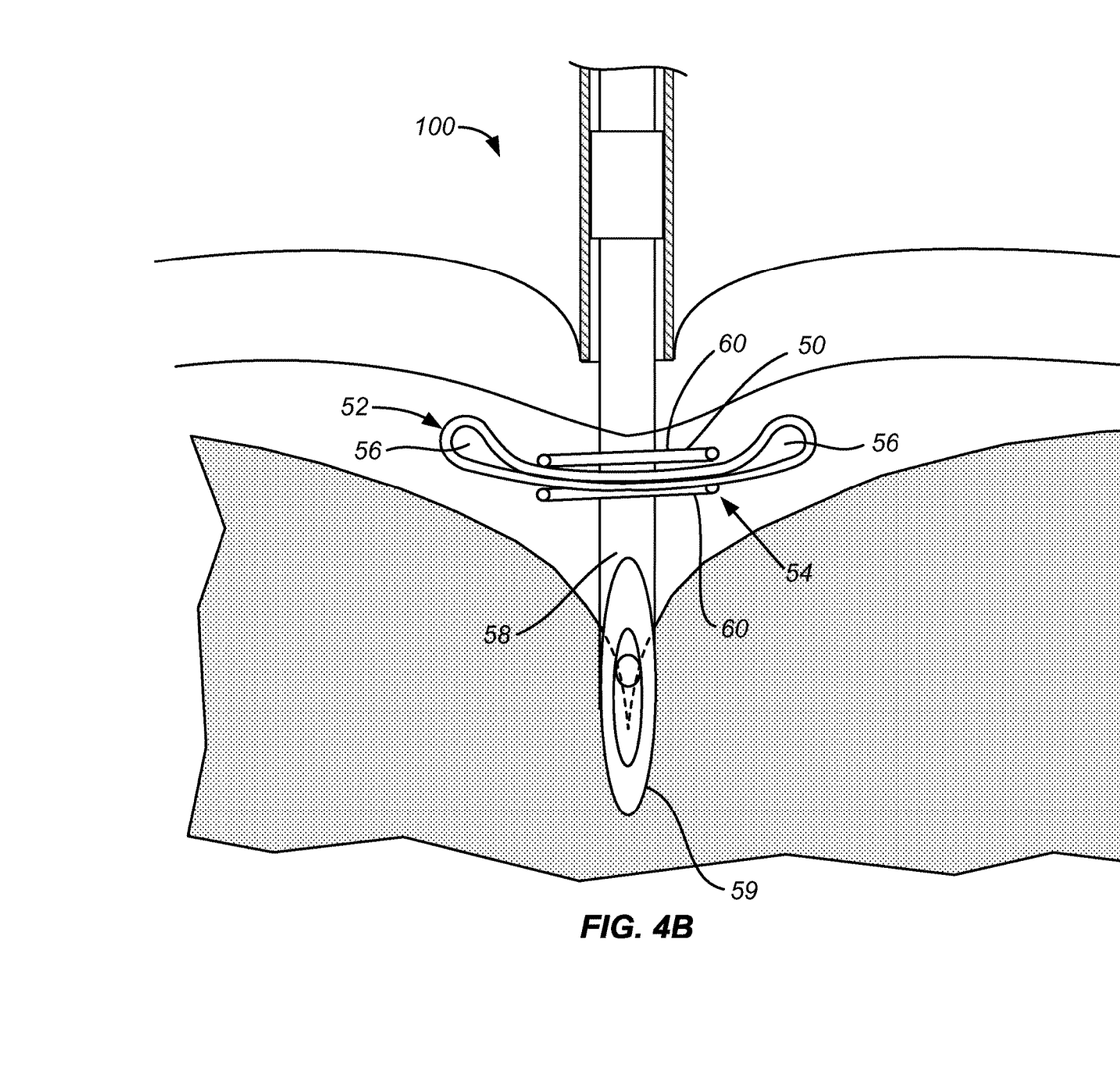

One example of a device or implant for facilitating vessel collapse is illustrated in FIGS. 4A and 4B. Device 50 is a helical clip which is designed for clamping/compressing a vein 52 and partially (or completely) flattening it when delivered and released. Device 50 is delivered using a dedicated delivery apparatus 100 (shown in FIGS. 5A-5B) by puncturing through penile tissue and opposing vein walls and positioning device 50 such that ends thereof are located above and below the external surfaces of opposite walls of the vein and a center section runs through the lumen of the vein.

Figure 6A:
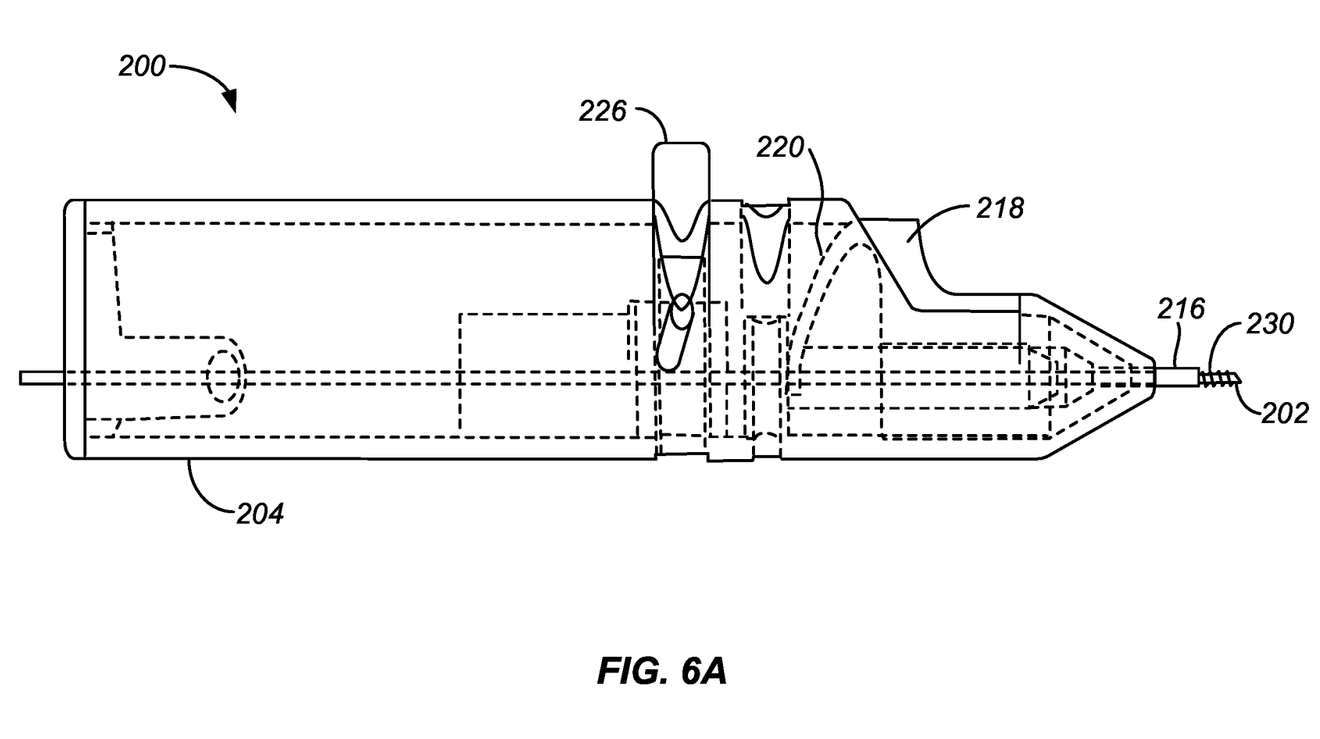
FIGS. 6A-6E illustrate a second embodiment of a compression implant delivery apparatus according to the present invention.
Figures 6B, 6E:
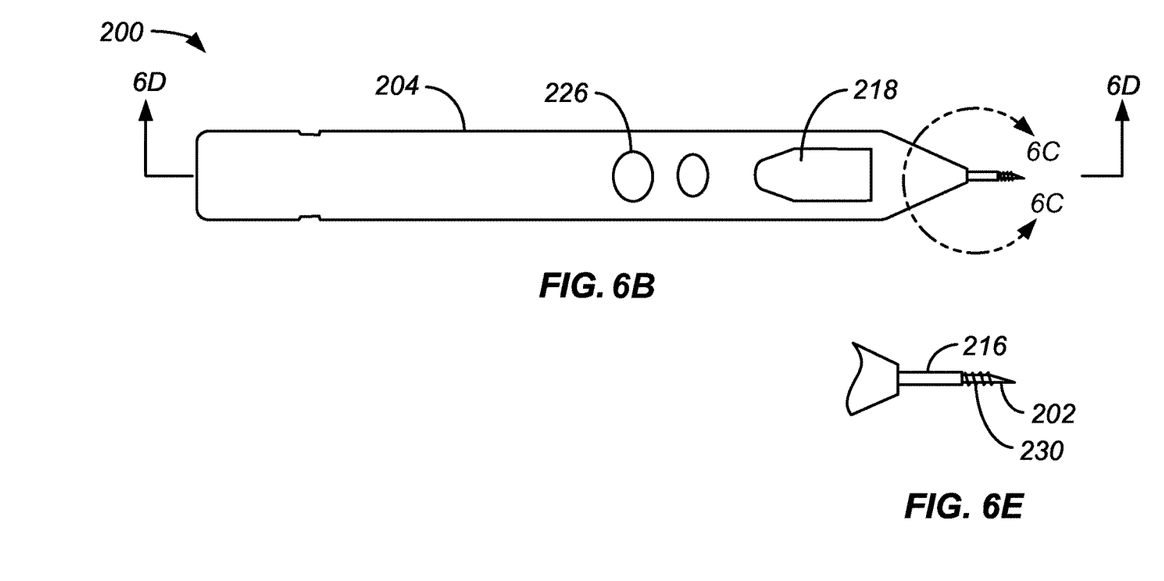
Figure 6C:
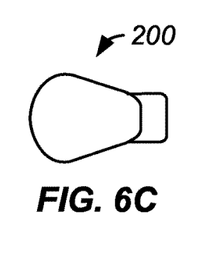
Figure 6D:
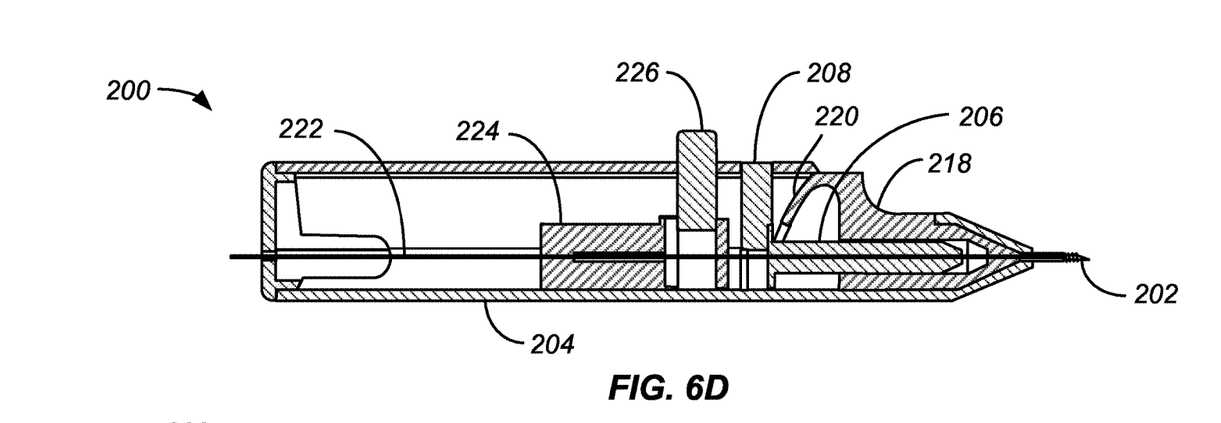

As shown in FIGS. 4A and 4B, the implant device 50 is illustrated as a helical clip having an elongated delivery configuration, as shown in FIG. 4A, and a foreshorted deployed configuration, as shown in FIG. 4b. The implant device 50 is mounted on a cannula 58 of the delivery apparatus 100 and is held open in the elongated configuration with oppsite ends of the helical clip detachably secured to spaced-apart locations on the cannula 58. In this confiugartion, individual coils 54 are typically spaced-apart 0.4 mm to 0.6 mm under tension. A tissue penetrating end 59 on cannula 58 is percutaneously inserted throug the skin of the penis downwardly into and through the superficial dorsal vein 52. Intially, the vein 52 is collpased by pressure from an over tube 216 (FIG. 6E). Once positioned and released, coils 54 elastically "recoil" to collapses the device 50 lengthwise to a coil spacing of 0 mm to 0.2 mm. The diameter of the coils simultaeously increases, forming upper and lower flanges 60, thereby approximating the walls of a vein 52, as shown in FIG. 4b. Once pressure on the vein increases (manual or hydrostatic), the vein further collapses to the "figure 8" shape as shown in FIG. 4b The tissue piercing end 59 of cannula 58 enables rotation and delivery of implant device 50 through walls of vein 52.

Once rotated into position (spanning vein 52), the implant device 50 is released from apparatus 100 and coils 54 collapse to partially collapse or "ovalize" vein 52. Under increased pressure on the vein, device 50 facilitates full flattening of a central region of vein 52 while leaving peripheral lumen regions 56 open to enable reduced flow through vein 52.

In an exemplary embodiment the coil is made of a Nitinol® wire. The diameter of the wire is about 0.1 mm. The coil has a diameter of about 1.5-2 mm. The number of coils is about three and the distance between coils is close to zero (when device 50 is not constrained). The coil is intended to be delivered thru the vein wall while the vein is compressed flat by a delivery device (further described hereinbelow), such that the distal 1 to 1.5 coils is threaded underneath the vein, and then the proximal coil(s) can be released above the vein.

The Delivery System:

The implant is tightly wound to a low or small profile around the tip of a tissue-penetrating element, such as a delivery needle or cannula, for insertion through the vessel. The outer diameter of the tissue-penetrating element is in the range of but not limited to 0.4 to 0.8 mm. An exemplary outer diameter of the tissue-penetrating element is 0.5 mm. The implant may be held at its distal end by an inner mandrel. The inner mandrel is typically an elongated member formed from a metal or polymeric, usually formed as a rod, tube, plunger, or the like. The inner mandrel is typically positioned within a lumen or passage within the elongated member near a distal end of the elongated member. The distal end of the inner mandrel comprises of a plug and a gap or hole, usually defining a small, typically 3 mm opening, where the implant may be inserted and secured to the elongated member by the plug. An over tube may be placed over the proximal coils of the implant to hold them under tension for delivery. The over tube is typically from from a polymer, metal, ceramic, or a combination thereof.

After the implant is inserted through the vessel and positioned at the right depth with about half the coils underneath the blood vessel and about half the coils over the blood vessel, the over tube can be pulled back to expose and release the proximal coils of the device. The inner mandrel can be pushed forward to release the distal end and thus the distal coils of the device. As seen in FIG. 4b, the device in its released position draws two sides of the vessel into close approximation and decreases the cross-section of the vessel to reduce blood flow. Even before releasing the implant device, the vein is compressed by the over tube 226 of the delivery system, see FIG. 4A. When released, the implant device elastically assumes its deployed configuration to maintain the compressed shape of the vessel 52.

Figure 5A:
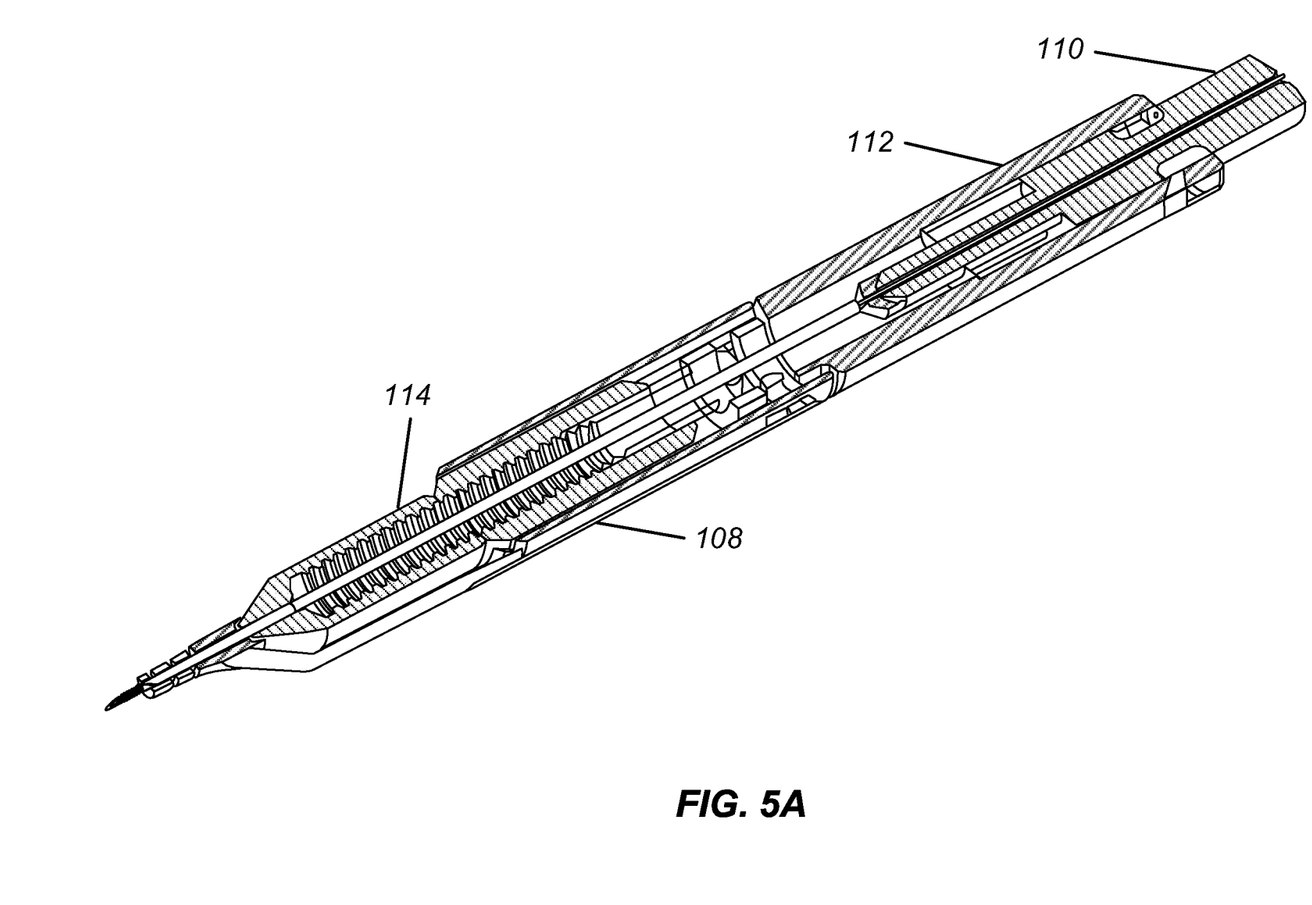
FIGS. 5A-5C illustrate a first embodiment of a compression implant delivery apparatus according to the present invention.
Figure 5B:
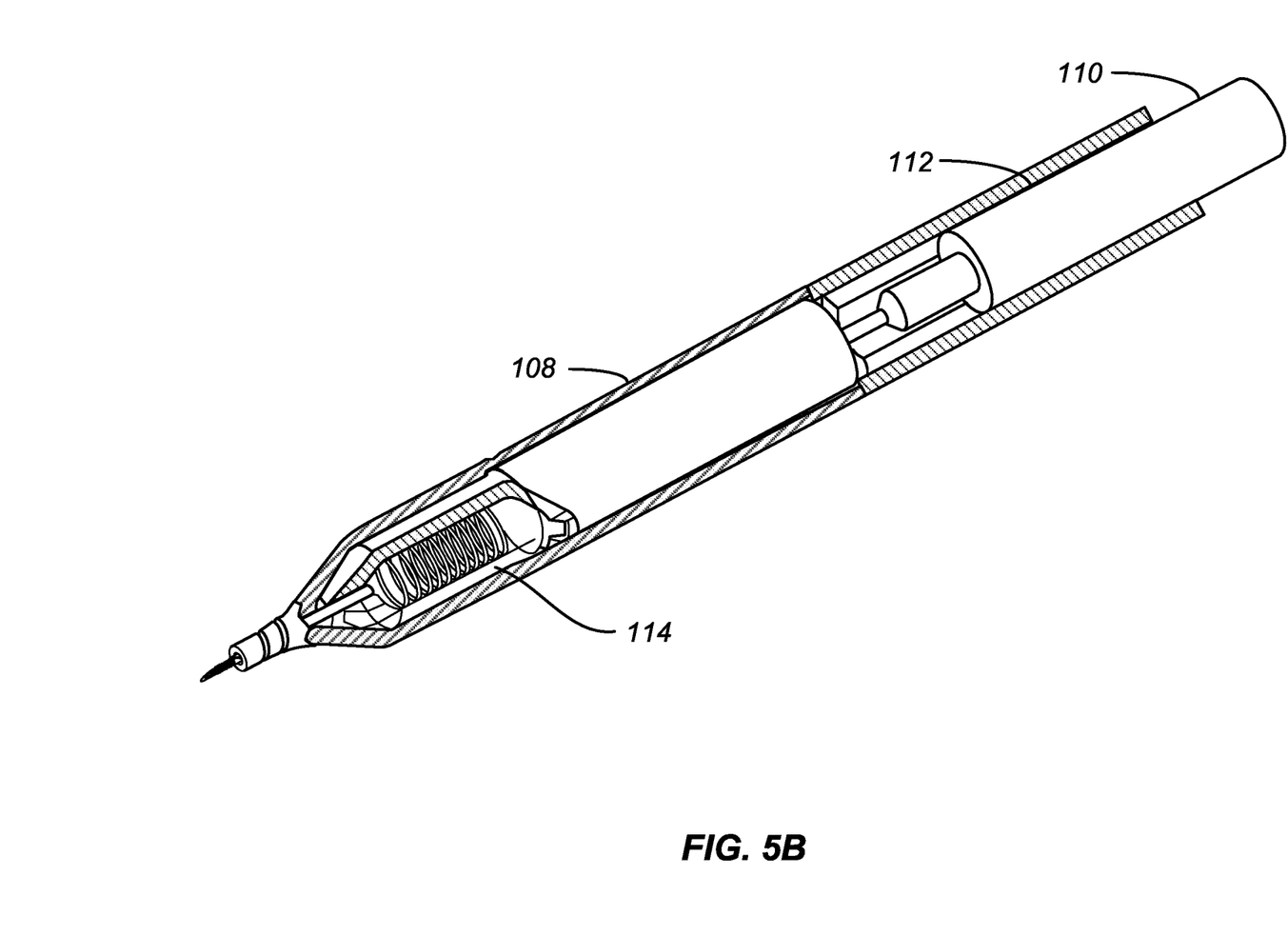
Figure 5C:
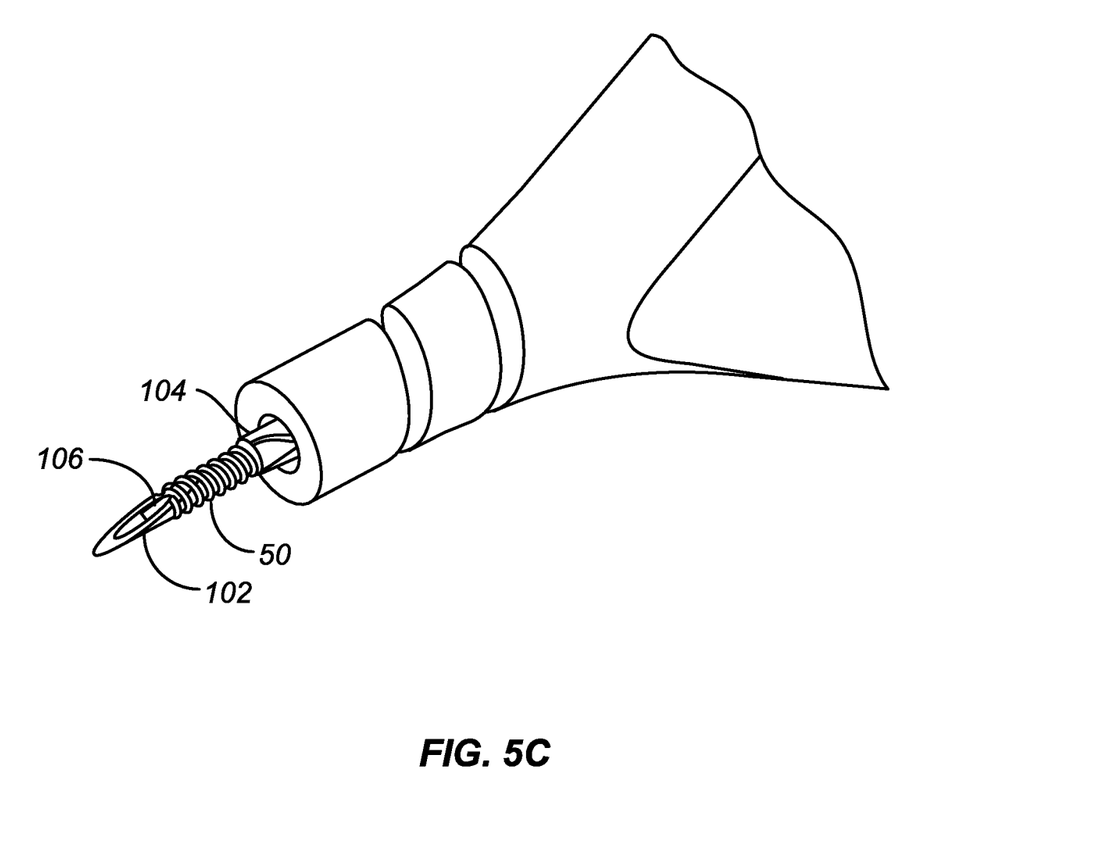

As is shown in FIGS. 5A-C apparatus 100 includes a needle cannula 102 over which device 50 (also referred to herein as coil 50) is tightly wrapped (FIG. 5c). Cannula 102 has a diameter of about 0.5 mm, and thus when wrapped thereupon the coils 50 stretch to about 3 mm-4 mm length and has about six to eight coils. Apparatus 100 further includes an over tube 104 holding the proximal end of coil 50 and an inner tube 106 holding the distal end of coil 50.

Apparatus 100 is inserted through the penile tissue and both vein walls to position coil 50 through the vein. At this depth the distal end of housing 108 of apparatus 100 compresses the vein flat. Blood flowing out at the top of inner tube 106 serves as an indication for correct depth. The distal end of coil 50 is then released by pressing knob 110 thereby moving inner tube 106 distally and unlocking the distal end of coil 50. The distal 1-1.5 coils of coil 50 are then threaded by holding the housing 108 while rotating knob 112 about 3 turns. At the end of this step the distal 1-1.5 coils are anchored underneath the vein. The number of rotations is limited by a counter 114 that can move up knob 112 three times the thread lead angle. Outer tube 104 is then rotated about one third of a turn using knob 114 of outer tube 104 to release the proximal end of coil 50.

Referring to FIGS. 6A-6E, an alternative design for a delivery device 200 includes a cannula 202 affixed to a distal end of an applicator body 204 to prevent relative movement therebetween. Typically, the cannula 200 is glued or otherwise fixedly secured to a cannula holder 206, and a cannula holder pin 208 fixes the cannula holder 206 to the applicator body 204. The cannula 202 has a stopper about 2 mm from a cannula opening that stops a proximal portion of implant coil 230 from being stretched while an over tube 216 (FIG. 6e) is being pulled back. The over tube 216 is attached to a sliding knob 218, preferably using adhesive. The sliding knob 218 can be pulled by an operator to proximally retract the over tube 216 and release the proximal-most coils of the device. The sliding knob comprises a spring element 220, either integral as illustrated or non-integral, which provides a force to bias the sliding knob 218 toward the distal end of the applicator body 204. The operator can thus draw the sliding knob 218 proximally to proximally retract the over tube 216, typically by about 4 mm, to expose and release the proximal coils of the coil implant 230.

An inner mandrel 222 is attached to an inner mandrel holder 224, which is positioned within the applicator body 204 proximal to the cannula holder 208. The inner mandrel holder 224 typically comprises an angular channel. A push knob 226 is placed within the inner mandrel holder 224, and the push knob 226 typically comprises of a pin that engages the angular channel which can push the inner mandrel holder 224 about 1.5 mm in the distal direction when the push knob 226 is pressed down to release the distal end of the device.

Thus, the implant 330 can be delivered in three basic steps. Step 1: Insert device through the target vessel and position so that about half the coils are located underneath the blood vessel and about half the coils are positioned above the blood vessel. Step 2: Draw the sliding knob 218 proximally to retract the over tube 216 to release the proximal-most coils of the device. Step 3: Press down the push knob 226 to push the inner mandrel and release the distal end of the implant.

While preferred embodiments of the present invention have been shown and described herein; it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for controlling blood flow through a vein, said system comprising:
    (a) a clip being sized and configured for compressing a region of the vein when positioned therethrough to reduce blood flow through the vein; and
    (b) a delivery device comprising a needle cannula, an over tube disposed over a proximal portion of the cannula, and an inner tube within a lumen of the needle cannula, said needle cannula having a tissue-penetrating distal end for penetrating tissue overlying a vein and delivering clip through said walls of the vein;
    wherein said clip comprises an elongated coil which is wrapped tightly about an outer surface of the needle cannula in a delivery configuration and wherein said over tube holds a proximal end of the coil and the inner tube holds the distal end of the coil in said delivery configuration; and
    wherein the over tube is configured to be reacted to release the proximal end of the coil and the inner tube is configured to be retracted to release the distal end of the coil, wherein the coil elastically recoils and foreshortens to form an upper flange configured to engage an upper wall of the vein and a lower flange configured to engage a lower wall of the vein.

2. The system of claim 1, wherein said clip is fabricated from a shape memory material capable of assuming a tissue compressive shape following delivery.

3. The system of claim 1, wherein said clip is configured for facilitating collapse of said vein under external pressure applied thereto.

4. The system of claim 1, wherein the elongated coil is configured to elastically recoil so that a length of the elongated coil foreshortens and the diameter of individual coils increases.

5. The system of claim 4, wherein the needle cannula has a diameter of about 0.5 mm and the clip has about six to eight coils which extend over a length of about 3 mm to 4 mm.

6. A method of controlling blood flow through a vein comprising:
    (a) delivering a clip having two ends through walls of the vein, wherein the clip is in an elongated coil when delivered through the walls of the vein
    (b) releasing one end of the coil above an upper wall of the coil and another end of the coil below a lower wall of the vein, wherein the coil elastically recoils and foreshortens to form an upper flange engaging the upper wall of the vein and a lower flange engaging a lower wall of the vein to thereby compress a middle region of the vein and reduce flow therethrough.

7. The method of claim 6, wherein said clip is configured for facilitating collapse of said vein under external pressure applied thereto.

8. The method of claim 6, wherein the clip is initially constrained over an outer surface of a needle cannula and wherein delivering the clip comprises penetrating the needle cannula through the walls of the vein to partially collapse the walls prior to releasing the one and other ends of the clip.

9. The method of claim 8, wherein an over tube on the needle cannula engages the upper wall of the vein as the needle cannula is penetrated.

10. The method of claim 9, wherein releasing the one end of the coil above the upper wall comprises retracting the over tube that holds the one end of the coil and releasing the other end of the coil comprises retracting an inner tube that holds the other end of the coil.

11. The method of claim 6, wherein the upper flange and the lower flange are located on the walls on the vein so that open lumens are left on each side of the vein to provide controlled blood flow.

* * * * *